United States Patent [19]

Kazumi et al.

[11] Patent Number: 5,125,982
[45] Date of Patent: Jun. 30, 1992

[54] METHOD OF CLEANING HARD CONTACT LENSES

[75] Inventors: Ogata Kazumi, Toyonaka; Kazumichi Ushio; Hisayuki Nakayama, both of Nishinomiya, all of Japan

[73] Assignee: Senju Pharmaceutical Co., Ltd., Osaka, Japan

[21] Appl. No.: 744,376

[22] Filed: Aug. 13, 1991

[30] Foreign Application Priority Data

Aug. 15, 1990 [JP] Japan .................................. 2-215395

[51] Int. Cl.$^5$ ................................................ B08B 3/08
[52] U.S. Cl. .......................................... 134/26; 134/42
[58] Field of Search ..................................... 134/26, 42

[56] References Cited

FOREIGN PATENT DOCUMENTS 196075 3/1985 European Pat. Off. .
56-8333 2/1981 Japan .
2101350 5/1981 United Kingdom .

*Primary Examiner*—Theodore Morris
*Assistant Examiner*—Zeinab El-Arini
*Attorney, Agent, or Firm*—Wenderoth, Lind & Ponack

[57] ABSTRACT

The object of the invention is to provide a method of cleaning a hard contact lens which is easy to use, excellent in the cleaning effect and then does not affect the lens material disadvantageously. The method of cleaning a hard contact lens is characterized in that the hard contact lens adhered with soil is immersed in a mixture of an aqueous solution of a permanganate salt and an aqueous solution of a mild reducing substance.

10 Claims, No Drawings

METHOD OF CLEANING HARD CONTACT LENSES

BACKGROUND OF THE INVENTION

Hard contact lenses now on market may be broadly classified into two groups. Those classified in one group are hitherto known hard contact lenses prepared from methyl methacrylate (MMA) as their principal material, which have no oxygen permeability. Hard contact lenses classified in the other group are recently developed ones prepared from silicone resin, fluoride resin or cellulosic material as their principal material, which have good oxygen permeability. Although such oxygen permeable hard contact lenses are recognized as more advantageous in their fitness on the eye than hitherto known ones, it is known that the oxygen permeable hard contact lenses are liable to be soiled, which is one of their defects. Being less susceptible to soiling, even the hitherto known hard contact lenses also become soiled caused from the deposit of eye discharges, proteinous substances, saccharides, mucosaccharides or inorganic substances, if such hard contact lenses are worn on the eye for a long period of time. Such is known as an inevitable defect of the hard contact lenses. It is known that, if the soiled contact lens is worn on the eye for a long period of time, the soil not only irritates the eye but also becomes the cause of growth of bacteria or fungi adhered on the contact lens utilizing these soils as their nutrient source to cause serious injuries to the eye. Thus, the removal of the soils adhered on the contact lens is an important problem to be solved. To remove such soil and to prevent such injuries, therefore, a variety of cleaning solutions have been proposed and employed. These cleaning solutions, however, have disadvantages in that they give harmful effect to the lens and/or an unclear end point of the cleaning is observed. Further, many of such cleaning solutions are not potent enough to clean a heavily soiled hard contact lens and particularly, as far as proteinous soils are concerned, there has not been known any effective method for cleaning hard contact lenses.

BRIEF SUMMARY OF THE INVENTION

The present invention relates to a method of cleaning contact lenses. More particularly, the invention relates to a method of cleaning a hard contact lens characterized in that the hard contact lens is immersed in a mixture of an aqueous solution of a permanganate salt and an aqueous solution of a mild reducing substance.

DETAILED DESCRIPTION

The present inventors endeavored to establish a cleaning method for hard contact lenses which would provide a powerful cleaning effect and, yet, be lenient on the lenses and found surprisingly that hard contact lenses can be advantageously cleaned with a mixture of an aqueous solution of a permanganate salt and an aqueous solution of a mild reducing substance.

The present invention is therefore directed to a method of cleaning a hard contact lens characterized in that the hard contact lens is immersed in a mixture of an aqueous solution of a permanganate salt and an aqueous solution of a mild reducing substance. While hard contact lenses are either oxygen-permeable or nonpermeable as aforementioned, the cleaning method of the present invention is applicable to both kinds of lenses.

In the cleaning method of the invention, the hard contact lens to be cleaned is immersed in a mixture of an aqueous solution of a permanganate salt and an aqueous solution of a mild reducing substance. The cleaning method of the invention can be practiced generally at room temperature and does not require any further procedure such as heating or stirring.

The permanganate salt to be used in the cleaning method of the invention may be any of the corresponding alkali metal salts, such as sodium and potassium salts, alkaline earth metal salts such as calcium and magnesium salts, and so on. Particularly preferred is potassium permanganate. The permanganate concentration of said aqueous permanganate solution can be appropriately chosen according to the kind of such salt, the kind of hard contact lens to be cleaned, the type and degree of soil to be removed, etc. and may range generally from about 0.01 to 5 percent, preferably from about 0.15 to 1.5 percent.

On the other hand, said mild reducing substance may be any substance that has mild reducing activity. However, mildly reducing organic acids such as citric acid, tartaric acid and succinic acid or mildly reducing saccharides such as xylose, glucose, mannose, galactose, ribose, etc. are preferred.

These reducing substances can be used either singly or in combination. The concentration of such mild reducing substance in aqueous solution is desirably just sufficient to reduce the permanganate salt mentioned above and the amount necessary to give such concentration can be easily found by stoichiometric calculation. The aqueous solution of such a mild reducing substance is controlled at a pH of about 2 through 7, preferably about 2 through 5. If necessary, the aqueous solution of such a mild reducing substance may further contain a preservative such as benzalkonium chloride, chlorhexidine, chlorobutanol.

Furthermore, in the cleaning method of the present invention, a surfactant can be used simultaneously. A surfactant has the advantage of removing the contamination by lipids such as oil at the same time, compared with the case of their absence. It is desirable that the surfactant is a nonionic, an anionic or an amphoteric one.

As the nonionic surfactant, polyglycerin fatty acid esters such as decaglyceryl monolaurate, polyoxyethylene alkyl ethers such as polyoxyethylene (25) lauryl ether, polyoxyethylene polyoxypropylene alkyl ethers such as polyoxyethylene polyoxypropylene cetyl ether, polyoxyethylene alkylphenyl ethers such as polyoxyethylene (30) octylphenyl ether are preferred, and further, polyoxyethylene sorbit fatty acid esters, polyoxyethylene alkyl amines, polyoxyethylene glycerin fatty acid esters, polyoxyethylene polyoxypropylene alkyl ethers, etc. can be also used.

As the anionic surfactant, alkyl sulfates such as sodium lauryl sulfate, N-acyl amino acids such as sodium N-lauroyl sarcosinate, N-acyl methyltaurates such as sodium N-cocoyl methyltaurates are preferred, and further, polyoxyethylene alkyl ether acetates, polyoxyethylene alkyl ether sulfates, alkyl sulfocarboxylates, etc. can be also used.

As the amphoteric surfactant, alkyl amino betaines and imidazolinium betaines are advantageous to use.

It is preferable that these surfactant are incorporated with an aqueous solution of the mild reducing substance, although an aqueous solution of the surfactant can be prepared separately and then mixed with an aqueous solution of said permanganate salt and an aqueous solution of said mild reducing substance. The concentration of surfactant used in the cleaning method of the present invention can be appropriately chosen according to the kind of surfactants, the kind and degree of soil to be removed, etc. and may range generally from about 0.05 to 5 percent, preferably from about 0.2 to 2 percent.

The hard contact lens thus cleaned by the cleaning method of the invention can be rinsed with, e.g., purified water, tap water, a hard contact lens preservative or soaking solution for hard contact lenses or the like in the usual manner, then can be put immediately on the eye.

As the soaking solution used herein, any of the known ones without irritation to the eye can be appropriately used.

The use of an aqueous permanganate salt solution in the cleaning of soft contact lenses has been disclosed in Japanese Patent Publication No. 8333/1981, for instance, but there has been no information at all on the cleaning of a hard contact lens with an aqueous permanganate salt solution. As already mentioned, the hard contact lens and the soft contact lens are dissimilar in chemical composition and, as such, behave differently towards the permanganate salt which is representative of powerful oxidizing agents. It was not until the finding by the present inventors that the behavior of permanganates towards hard contact lenses was ever elucidated and that it was ever found that these salts do not adversely affect the lens material and can therefore be used as cleaning agents for hard contact lenses.

In the cleaning method of the present invention, a mixture of an aqueous solution of said permanganate salt and an aqueous solution of said mild reducing substance is employed. Since the permanganate salt is a powerful oxidizing agent as is well known, it might be expected that mixing of a solution thereof with an aqueous solution of a reducing substance instantly sets off an interaction between the two agents to neutralize the system. However, when a mild reducing substance is selected as the reducing agent, the two agents remain stable in the mixed solution over a time period necessary for complete cleaning of the hard contact lens, with the surprising result that both oxidation and neutralization can be accomplished with a single mixed solution.

In the cleaning of a hard contact lens to which lipids has adhered, addition of surfactants is preferable, and nonionic and anionic ones are particularly effective for the purpose.

In the cleaning of a hard contact lens severely soiled with deposits of calcium, the pH of an aqueous solution containing said mild reducing substance is preferably controlled on the acidic side using an organic acid as the mild reducing agent and a particularly beneficial pH range is pH 2 to 5.

When an aqueous permanganate salt solution and an aqueous mild reducing substance solution are used independently, the hard contact lens is first immersed in an aqueous solution of the permanganate salt, which is a powerful oxidizing agent, and then treated with the reducing substance which is a neutralizing agent but it is then difficult to find the end-point of cleaning of the hard contact lens in the permanganate salt solution. Thus, it is necessary to set the permanganate cleaning time in accordance with the type of hard contact lens, the degree of fouling and other factors and, moreover, it is difficult to completely avoid the degradation of the lens material due to excessively prolonged immersion. The use of a mixture of such an aqueous permanganate solution and an aqueous solution of a mild reducing agent in accordance with the present invention offers the advantage that, provided that the proportions of the two agents are appropriately chosen, the end-point of treatment can be easily ascertained from the color of the mixed solution. Thus, the disappearance of the color characteristic of the permanganate salt from the mixed solution indicates the end-point of cleaning. It is, therefore, obvious that both setting of the cleaning time and control of the cleaning process are remarkably facilitated.

Furthermore, since the lens is cleaned with a mixture of an aqueous solution of the permanganate salt and an aqueous solution of the mild reducing substance in the method of the invention, the adverse influence of the permanganate salt as a powerful oxidizing agent can be well controlled, thus offering the advantage that, compared with the practice of immersing a hard contact lens in an aqueous solution of permanganate salt only, the degradation of the lens material can be held to a minimum.

TEST EXAMPLE

Test materials

A cleaning composition for hard contact lenses was prepared according to the following formula.

| No. 1 solution | |
|---|---|
| Potassium permanganate | 0.66% |
| Purified water | q.s. |
| No. 2 solution | |
| Citric acid | 2.0% |
| Glucose | 1.0% |
| Disodium hydrogen phosphate | 0.5% |
| Sodium hydroxide | q.s. |
| Purified water | q.s. |

The following four kinds of hard contact lenses were used in this experiment.

| Code | Lens material |
|---|---|
| A | Fluoro-silicone/acrylate |
| B | Cellulose acetate butyrate |
| C | Polymethyl methacrylate |
| D | Silicone/acrylate |

Method

Two milliliters each of No. 1 and No. 2 solutions were placed in a 5 ml vial and the test hard contact lens, fouled by wearing on the human eye, was immersed in the mixed solution. When the solution had become colorless, the hard contact lens was taken out and rinsed with a soaking solution.

For each of the four kinds of hard contact lenses, the diameter and base curve before treatment were measured beforehand and the above treatment was repeated 50 times. Thereafter, the diameter and base curve were measured again. The results are shown below.

Results

| Test lens | Before treatment | | After 50th treatment | |
|---|---|---|---|---|
| | Diameter | Base curve | Diameter | Base curve |
| A | 8.8 | 7.9 | 8.8 | 7.9 |
| B | 8.9 | 8.0 | 8.9 | 8.0 |
| C | 8.8 | 7.5 | 8.8 | 7.5 |
| D | 8.9 | 7.8 | 8.9 | 7.8 |

(unit: mm)

Despite the fact that the concentration of the cleaning composition used in this experiment was by far higher than the concentration recommended for practical use and the test condition was as severe as 50 immersions, all the test hard contact lenses remained unchanged in diameter or in base curve. No change was found either, in any of gross appearance, angle of contact and lens power.

EXAMPLE 1

| No. 1 solution | |
|---|---|
| Potassium permanganate | 0.3% |
| Purified water | q.s. |
| No. 2 solution | |
| Citric acid | 2% |
| Tartaric acid | 2% |
| Succinic acid | 2% |
| Sodium hydroxide | q.s. |
| Purified water | q.s. |
| | (pH 3.5) |

Two milliliters each of No. 1 and No. 2 solutions were mixed in a 5 ml vial and an oxygen-permeable hard contact lens (Elcon ® Ex-O₂), fouled by wearing on the human eye, was immersed therein. When the solution had become colorless, the hard contact lens was rinsed with a soaking solution.

Macroscopic observation revealed that the hard contact lens treated with the cleaning composition of this example had been thoroughly freed of soil and was crystal-clear.

EXAMPLE 2

| No. 1 solution | |
|---|---|
| Potassium permanganate | 0.2% |
| Purified water | q.s. |
| No. 2 solution | |
| Glucose | 1.0% |
| Citric acid | 0.5% |
| Disodium hydrogen phosphate | 0.5% |
| Sodium hydroxide | q.s. |
| Purified water | q.s. |
| | (pH 3.5) |

Two milliliters each of No. 1 and No. 2 solutions were mixed in a 5 ml vial and an oxygen-permeable hard contact lens (Elcon ® EX-O₂), fouled by wearing on the human eye, was immersed therein. When the solution had become colorless, the hard contact lens was rinsed with a soaking solution.

Macroscopic observation revealed that the hard contact lens treated with the cleaning composition of this example had been thoroughly freed of soil and was crystal-clear.

EXAMPLE 3

| No. 1 solution | |
|---|---|
| Potassium permanganate | 0.03% |
| Purified water | q.s. |
| No. 2 solution | |
| Citric acid | 0.2% |
| Tartaric acid | 0.1% |
| Disodium hydrogen phosphate | 0.05% |
| Sodium hydroxide | q.s. |
| Purified water | q.s. |
| | (pH 3.5) |

Two milliliters each of No. 1 and No. 2 solutions were mixed in a 5 ml vial and an oxygen-permeable hard contact lens (Elcon ® EX-O₂), fouled artificially with 0.1% of lysozyme chloride, was immersed therein. When the solution had become colorless, the hard contact lens was rinsed with soaking solution.

Macroscopic observation revealed that the hard contact lens treated with the cleaning composition of this example had been thoroughly freed of soil and was crystal-clear.

EXAMPLE 4

| No. 1 solution | |
|---|---|
| Potassium permanganate | 0.03% |
| Purified water | q.s. |
| No. 2 solution (A) | |
| Citric acid | 0.2% |
| Tartaric acid | 0.1% |
| Polyoxyethylene (25) lauryl ether | 0.5% |
| Disodium hydrogen phosphate | 0.05% |
| Sodium hydroxide | q.s. |
| Purified water | q.s. |
| | (pH 3.5) |

In No. 2 solution (A), polyoxyethylene (25) lauryl ether (0.5%) was replaced with decaglyceryl monolaurate (0.5%) polyoxyethylene polyoxypropylene cetyl ether (0.5%), polyoxyethylene (30) octylphenyl ether (0.5%), sodium lauryl sulfate (1.0%), sodium N-lauroyl sarcosinate (0.5%) or sodium N-cocoyl methyltaurates (2.0%) to prepare No. 2 solution (B), (C), (D), (E) and (F) respectively.

Two milliliters each of No. 1 solution and No. 2 solution (A), (B), (C), (D), (E) or (F) were mixed in a 5 ml vial and then an oxygen-permeable hard contact lens (Elcon ® EX-O₂), fouled with artificial soil[1]), was immersed therein. When the solution had become colorless, two or three drops of the colorless mixture were distilled to both faces of the hard contact lens. And the lens was cleaned by rubbing softly and then rinsed with water.

Macroscopic observation revealed that the hard contact lens treated with the cleaning compositions of this example had been thoroughly freed of soil and was crystal-clear.

EXAMPLE 5

| No. 1 solution | |
|---|---|
| Potassium permanganate | 0.03% |
| Purified water | q.s. |
| No. 2 solution | |
| Citric acid | 0.2% |
| Tartaric acid | 0.1% |
| Decaglyceryl monolaurate | 0.5% |

| -continued | |
|---|---|
| N-Sodium lauroyl sarcocine | 0.5% |
| N-Sodium cocoyl methyl taurine | 2.0% |
| Disodium hydrogen phosphate | 0.05% |
| Sodium hydroxide | q.s. |
| Purified water | q.s. |

Two milliliters each of No. 1 and No. 2 solutions were mixed in a 5 ml vial and an oxygen-permeable hard contact lens (Elcon® EX-O$_2$), fouled with artificial soil[1]), was immersed therein. When the solution had become colorless, two or three drops of the colorless mixture were distilled to both faces of the hard contact lens. And the lens was cleansed by rubbing softly and then rinsed with water.

Macroscopic observation revealed that the hard contact lens treated with the cleaning composition of this example had been thoroughly freed of soil and was crystal-clear.

| (1) Artificial soil | |
|---|---|
| Myristic acid | 0.2% |
| Oleic acid | 0.1% |
| Tristearin | 0.5% |
| Cholesterol stearate | 0.5% |
| Cholesterol | 2.0% |
| Squalene | 0.05% |

What is claimed is:

1. A method of cleaning a hard contact lens characterized in that the hard contact lens is immersed in a mixture of an aqueous solution of a permanganate salt and an aqueous solution of a mild reducing substance.

2. A method of cleaning a hard contact lens according to claim 1, wherein the mild reducing substance is a reducing organic acid.

3. A method of cleaning a hard contact lens according to claim 1 or 2, wherein the mild reducing organic acid is one or more substances selected from the group consisting of citric acid, tartaric acid and succinic acid.

4. A method of cleaning a hard contact lens according to claim 1, wherein the mild reducing substance is a mild reducing saccharide.

5. A method of cleaning a hard contact lens according to claim 1 or 4, wherein the mild reducing saccharide is one or more substances selected from the group consisting of xylose, glucose, mannose, galactose and ribose.

6. A method of cleaning a hard contact lens according to claim 1, 2, 3, 4 or 5, wherein a mixture of an aqueous solution of a permanganate salt and an aqueous solution of mild reducing substance contains a surfactant.

7. A method of cleaning a hard contact lens according to claim 6, wherein the surfactant is a nonionic surfactant.

8. A method of cleaning a hard contact lens according to claim 7, wherein the nonionic surfactant is one or more substances selected from the group consisting of polyglyceride, polyoxyethylene alkyl ether, polyoxyethylene polyoxypropylene alkyl ether and polyoxyethylene alkylphenyl ether.

9. A method of cleaning a hard contact lens according to claim 6, wherein the surfactant is an anionic surfactant.

10. A method of cleaning a hard contact lens according to claim 9, wherein the anionic surfactant is one or more substances selected from the group of alkyl sulfonic ester, N-acyl amino acid and N-acyl methyl taurine salt.

* * * * *

UNITED STATES PATENT AND TRADEMARK OFFICE
CERTIFICATE OF CORRECTION

PATENT NO. : 5,125,982
DATED : June 30, 1992
INVENTOR(S) : KAZUMI OGATA, KAZUMICHI USHIO, HISAYUKI NAKAYAMA It is certified that error appears in the above-identified patent and that said Letters Patent is hereby corrected as shown below:

On the title page, Item [19]     change "Kazumi et al." to —Ogata et al.—.

Item: [75], change "Ogata Kazumi" to —Kazumi Ogata—.

Column 8, line 27, change "polyglyceride" to —polyglycerine fatty acid ester—.

Column 8, lines 35 and 36, change "sulfonic ester" to —sulfate—.

Column 8, lines 36 and 37, change "taurine salt" to —taurate—.

Signed and Sealed this

Sixteenth Day of November, 1993

Attest:

BRUCE LEHMAN

Attesting Officer     Commissioner of Patents and Trademarks